US00PP24835P3

(12) United States Plant Patent
Glen

(10) Patent No.: US PP24,835 P3
(45) Date of Patent: Sep. 2, 2014

(54) NECTARINE TREE NAMED 'PEARLICIOUS XVII'

(50) Latin Name: *Prunus persica*
Varietal Denomination: Pearlicious XVII

(71) Applicant: Lowell Glen, Le Grand, CA (US)

(72) Inventor: Lowell Glen, Le Grand, CA (US)

( * ) Notice: Subject to any disclaimer, the term of this patent is extended or adjusted under 35 U.S.C. 154(b) by 6 days.

(21) Appl. No.: 13/694,612

(22) Filed: Dec. 13, 2012

(65) Prior Publication Data

US 2014/0173791 P1 Jun. 19, 2014

(51) Int. Cl.
*A01H 5/00* (2006.01)

(52) U.S. Cl.
USPC ..... Plt./188

(58) Field of Classification Search
USPC ..... Plt./188
See application file for complete search history.

(56) References Cited

U.S. PATENT DOCUMENTS

PP8,948 P 10/1994 Bradford
PP9,359 P 11/1995 Bradford
PP18,696 P2 4/2008 Bradford

*Primary Examiner* — Kent L Bell

(57) ABSTRACT

The present invention relates to a new and distinct variety of nectarine tree, *Prunus persica,* broadly characterized by a medium size, moderately vigorous, hardy, self-fertile, productive and regular bearing tree. The variety blooms in the late season and requires about 650 chilling hours. The fruit matures under the ecological conditions described in early September, with first picking on Sep. 2, 2012. The fruit is large in size, fairly globose in shape, clingstone in type, firm and melting in texture, white in flesh color, mostly red in skin color, and a tasty balance of light acid and sugar in flavor.

1 Drawing Sheet

Botanical classification: *Prunus persica.*
Variety denomination: 'Pearlicious XVII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of nectarine tree, which has been denominated varietally as 'Pearlicious XVII'.

In the flowering season of 2003 I hybridized a first generation cross using '28P1130' (unpatented) yellow flesh freestone nectarine as the selected seed parent and '1P861' (unpatented) white flesh nectarine as the selected pollen parent. The fruit of this cross was gathered in the summer of 2003, and the seeds were removed from the fruit, germinated, stratified, and grown as seedlings on their own root in my greenhouse. Upon reaching dormancy the following winter, the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of nectarine tree, I asexually reproduced it by budding and grafting in the experimental orchard described above, and such reproduction of tree and fruit characteristics were true to the original tree in all respects. The reproduction of the variety included the use of 'Nemaguard' (unpatented) rootstock upon which the present variety was compatible and true to type.

While both of the parents are unpatented, the '1P861' nectarine was itself a first generation cross between 'Bright Pearl' (U.S. Plant Pat. No. 9,359) white flesh nectarine as its selected seed parent and 'Diamond Ray' (U.S. Plant Pat. No. 8,848) yellow flesh nectarine as its selected pollen parent.

The present variety is similar to its grand-parent, 'Bright Pearl' nectarine (U.S. Plant Pat. No. 9,359) by being self-fertile and producing white flesh clingstone nectarines, but is quite distinguished therefrom by having a sweet instead of bitter kernel and by maturing about fifty days later.

The present variety is similar to its pollen grand-parent, 'Diamond Ray' nectarine (U.S. Plant Pat. No. 8,948) by being self-fertile and producing clingstone nectarines, but is quite distinguished therefrom by having globose instead of reniform leaf glands and producing fruit that is white instead of yellow in flesh color and that matures about sixty days later.

The present variety is similar to its seed parent, '28P1130,' in several aspects, such as producing nectarines that are firm and mostly red in skin color, but it is quite distinguished therefrom by producing nectarines that are white flesh instead of yellow flesh, that are clingstone instead of freestone, and that ripen about ten days later.

The present variety is similar to its pollen parent, '1P861,' in several aspects, such as producing nectarines that are firm, clingstone, and mostly red in skin color, but it is quite distinguished therefrom by producing nectarines that ripen about twenty-five days later.

The present variety is most similar to 'Snow Pearl' (U.S. Plant Pat. No. 14,695) nectarine by having a moderately vigorous tree, having globose leaf glands, being self-fertile, and producing white flesh clingstone nectarines that are firm, are mostly red in skin color, and have a sweet kernel, but is distinguished therefrom by producing fruit that is larger in size, matures about fifteen days later, is somewhat sweeter, and is a balance of light acid and sugar rather than sub-acid in flavor.

SUMMARY OF VARIETY

In summary, the present nectarine variety is characterized by a medium size, moderately vigorous, hardy, self-fertile, productive and regular bearing tree. The variety blooms in the late season and requires about 650 chilling hours. The fruit matures under the ecological conditions described in early September, with first picking on Sep. 2, 2012. The fruit is large in size, fairly globose in shape, clingstone in type, firm and melting in texture, white in flesh color, mostly red in skin color, and a tasty balance of light acid and sugar in flavor.

DRAWING

The accompanying photograph consists of four whole fruits positioned to display the characteristics of the skin color and form, one divided fruit to reveal the flesh and stone, two insets to reveal buds and a blossoms, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Sep. 10, 2012, on the original tree during its ninth growing season. The blossom and flower descriptions were made the previous blooming season. All major color code designations are by reference to the Inter-Society Color Council, National Bureau of Standards. Common color names are also used occasionally.

PARENTAGE

Seed parent: '28P1130' nectarine (unpatented).
Pollen parent: '1P861' nectarine (unpatented).

TREE

Size: Medium, reaching and maintaining a height of 10' [3.05 m.] and a spread of 6' [1.83 m.] after nine growing seasons utilizing typical dormant pruning.

Vigor: Moderately vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Approximate chilling requirement: 650 hours.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, reaching a maximum diameter of 4" [101.6 mm.] after the ninth growing season.

*Texture.*—Slightly shaggy.

*Bark color.*—A Light grayish brown [60. l.gy.Br] and Grayish brown [61. gy.Br] variegation with a few Brownish gray [64. brGy] crevices.

*Lenticels.*—Approximate Number Per Square Inch: 5. Color: Deep orange yellow [69. deep OY]. Average Size: ¼" [6.4 mm.] in length, 1/16" [1.6 mm.] in diameter. Shape: Eye-shaped, elongated.

Branches:

*Size.*—Diameter of main scaffold is 2¼" [57.2 mm.] measured 12" above the crotch, Diameter of limb is 1⅜" [34.9 mm.] measured 12" above the first fork.

*Texture.*—Smooth on first year wood, increasing roughness with age.

*Color.*—1st Year Wood Topside: Grayish red [19. gy.R]. 1st Year Wood Underside: Brilliant yellow green [116. brill.YG]. Second Year Wood: Grayish brown [61. gy.Br]. Third Year Wood: Light grayish brown [60. l.gy.Br].

*Lenticels.*—Number Per Square Inch: More than 30 on second year wood. Color: Dark orange yellow [72. d.OY]. Size: ⅛" [3.2 mm.] to 1/16" [1.6 mm.] in length on second year wood. Diameter is typically one fourth as much as the length. Shape: Eye-shaped, elongated.

Leaves:

*Size.*—Large. Average Length: 5⅜" [136.5 mm.]. Average Width: 1¾" [44.5 mm.].

*Arrangement.*—Alternate.

*Thickness.*—Medium.

*Form.*—Elliptical.

*Apex.*—Acuminate.

*Base.*—Young leaves are mostly acute, older leaves are rounded to obtuse.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ½" [12.7 mm.]. Average Thickness: 1/16" [1.6 mm.]. Color: Brilliant yellow green [116. brill.YG].

*Stipules.*—Number: Usually 2 per leaf, up to 6 per growing tip. Average Length: ⅜" [9.5 mm.]. Color: Moderate yellow green [120. m.YG] becoming Grayish brown [61. gy.Br] with maturity.

*Glands.*—Number: 1 to 4 per leaf. Position: Alternately positioned on petiole and base of blade. Size: Medium. Form: Globose on young leaves, becoming a reniform shape with age. Color: Brilliant yellow green [116. brill.YG] becoming Dark grayish brown [62. d.gy.Br] in the center with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.
*Tip color.*—Moderate purplish pink [250. m.pPk].

Flowers: Perfect, complete, perigynous, usually a single pistil, about thirty stamens, five sepal and petal locations alternately positioned.
*Type.*—Showy, large.
*Average flower diameter.*—1⅞" [47.6 mm.].
*Average flower depth.*—7/16" [11.1 mm.] when fully open.
*Number of petals.*—Mostly five, extra petal fragments or double blossoms are occasionally observed.
*Petal shape.*—Circular to oval.
*Petal margin.*—Entire, slightly wavy.
*Average petal diameter.*—¾" [19.1 mm.].
*Average petal length.*—13/16" [20.6 mm.].
*Petal apex.*—Rounded.
*Petal base.*—Rounded to somewhat truncate.
*Petal color.*—Pale pink [7. p.Pk] toward the apex, Deep purplish pink [248. deep pPk] toward the base on both sides.
*Anther color.*—Very red [11. v.R] over a Light yellow [86. l.Y] center at bloom onset.
*Stigma color.*—Pale yellow green [121. p.YG].
*Sepal color.*—Dark purplish red [259. d.pR] on the outer surface. The inner surface is a somewhat translucent Pinkish white [9. pk White] with both Grayish purplish red [262. gy.pR] and Vivid yellow green [116. brill.YG] areas visible.
*Sepal outer surface.*—Pubescent.
*Sepal length.*—5/16" [7.9 mm.].
*Sepal width.*—3/16" [4.8 mm.].
*Sepal apex.*—Rounded to elliptical.
*Sepal margin.*—Fairly smooth.
*Average pistil length.*—11/16" [17.5 mm.].
*Average stamen length.*—9/16" [14.3 mm.].
*Fragrance.*—Moderate.
*Blooming period.*—Medium to late, one day after 'September Bright' (U.S. Plant Pat. No. 13,475) nectarine.
*Onset of bloom.*—One percent on Feb. 27, 2012.
*Date of full bloom.*—Mar. 8, 2012.
*Duration of bloom.*—One to two weeks, dependent on ambient temperature.
*Number per cluster.*—1 to 3 with single flowers most common.

FRUIT

Maturity when described: Firm ripe, Sep. 10, 2012.
Date of first picking: Sep. 2, 2012.
Date of last picking: Sep. 16, 2012.
Size: Uniform, large.
*Average diameter axially.*—2⅞" [73.0 mm.].
*Average diameter across cheek plane.*—3" [76.2 mm.].
*Average diameter across suture plane.*—3" [76.2 mm.].
*Typical weight.*—9.7 ounces [274.9 grams].
Form: Uniform, globose and slightly compressed axially.
*Longitudinal section form.*—Round.
*Transverse section through diameter.*—Round.
Suture: Extends from the base, continues along the side, and ends just past the pistil point.
*Near the base.*—A shallow groove.
*Along the side.*—A shallow trough.
*Near the apex.*—A medium groove.
Ventral surface: Rounded, lipped toward the apex on both sides.
Lips: Slightly unequal.
Cavity: Flaring, slightly elongated in the suture plane, suture showing on one side, Yellowish white [92. yWhite] stem markings typical.
*Depth.*—⅝" [15.9 mm.].
*Breadth.*—1⅜" [34.9 mm.].
Base: Truncate.
Apex: Rounded, cordate if viewed parallel to the suture.
Pistil point: Some apical and some oblique, mostly depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in a dry season.
*Color.*—Dark red [16. d.R] mottled with Moderate pink [5. m.Pk] over a Yellowish white [92. yWhite] background with some Pale orange yellow [73. p.OY] freckling.
Flesh:
*Color.*—Greenish white [153. gWhite] to Yellowish white [92. yWhite] with Dark red [16. d.R] streaking next to the stone.
*Surface of pit cavity.*—Covered with Dark red [16. d.R] broken fibers when twisted from the stone.
*Amygdalin.*—Moderate.
*Juice.*—Abundant, rich.
*Texture.*—Firm, crisp, melting.
*Fibers.*—Abundant, fine.
*Ripens.*—Fairly even, slightly earlier at the apex.
*Flavor.*—A tasty balance of light acid and strong sugar, typically 20 brix.
*Aroma.*—Slight.
*Eating quality.*—Very good.

STONE

Type: Clingstone.
Form: Oval.
Hilum: Narrow.
Base: Truncate.
Apex: Acuminate.
Sides: Equal.
Surface: Irregularly furrowed near the apex, pitted toward the base.
Ridges: Jagged.
External color: Dark brown [59. d.Br].
Pit wall color when cracked: Moderate brown [58. m.Br].
Cavity surface color: Strong brown [55. s.Br].
Average pit wall thickness: 5/16" [7.9 mm.].
Average width: 1¼" [31.8 mm.].
Average length: 1¾" [44.5 mm.].
Average breadth: ⅞" [22.2 mm.].
Tendency to split: None observed.
Kernel:
*Form.*—Oval.
*Skin Color.*—Deep orange yellow [69. deep OY] when first removed.
*Pellicle color.*—Moderate brown [58. m.Br].
*Vein color.*—Moderate brown [58. m.Br].
*Taste.*—Sweet.

*Viable.*—Yes.
*Average width.*—9/16" [14.3 mm.].
*Average length.*—15/16" [23.8 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Snow Pearl' (U.S. Plant Pat. No. 14,695) nectarine by having a moderately vigorous tree, having globose leaf glands, being self-fertile, and producing white flesh clingstone nectarines that are firm, are mostly red in skin color, and have a sweet kernel, but is distinguished therefrom by producing fruit that is larger in size, matures about fifteen days later, is somewhat sweeter, and is a balance of light acid and sugar rather than sub-acid in flavor.

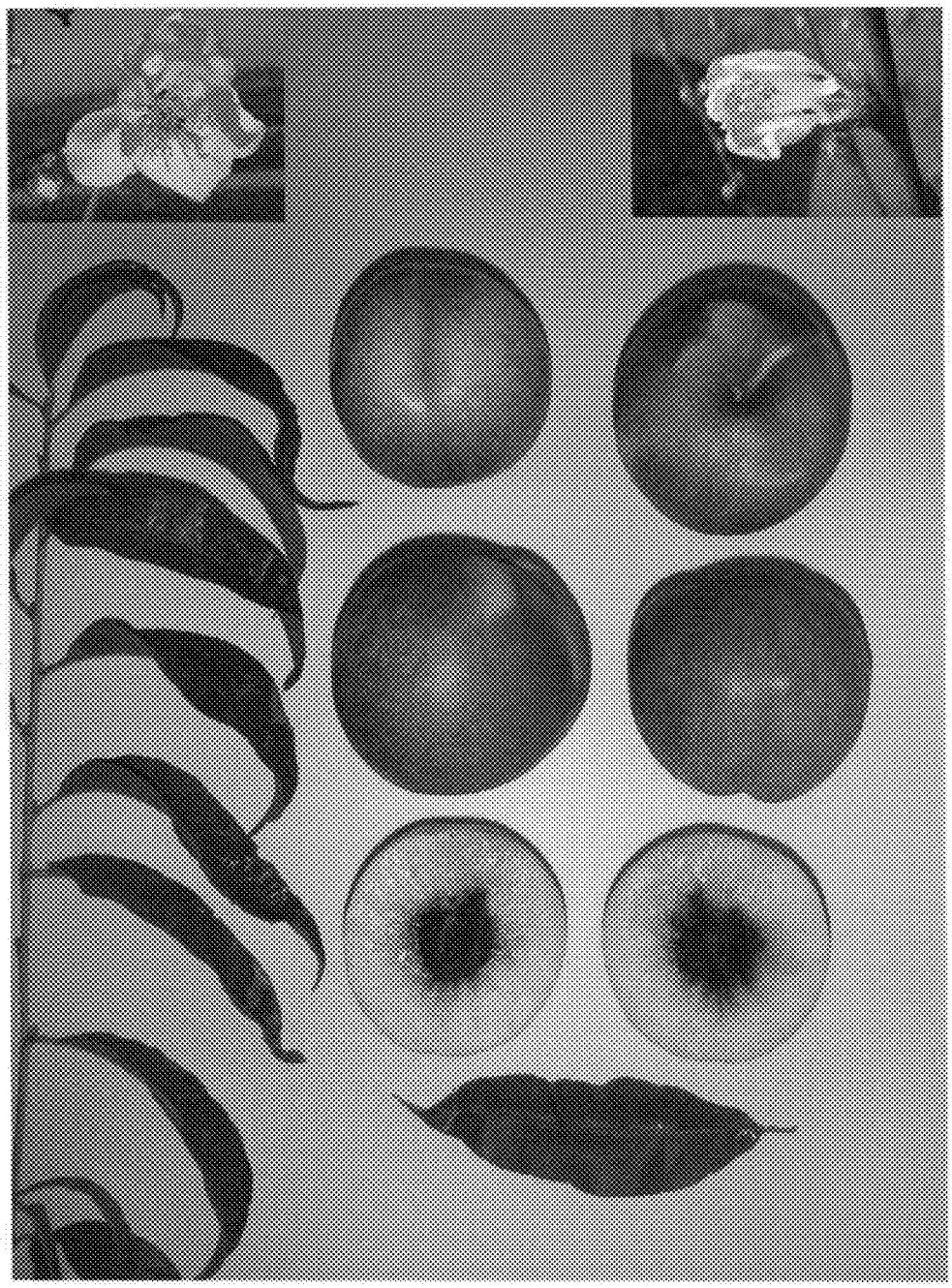

* * * * *